US00PP08926P

United States Patent [19]

Van der Salm

[11] Patent Number: Plant 8,926

[45] Date of Patent: Oct. 4, 1994

[54] LILIUM ROSE PARAMOUNT

[76] Inventor: Gerardus C. Van der Salm, 35306 NW. Toenjes Rd., Woodland, Wash. 98674

[21] Appl. No.: 186,699

[22] Filed: Jan. 25, 1994

[51] Int. Cl.[5] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing large upfacing flowers of excellent form and long persistence, both on the plant and as cut-flowers. The flowers of the new plant are particularly characterized by their large size and substance, their broad tepals, their completely upfacing orientation, their even medium pink coloration, their green nectaries with yellow papillose margins, and their deeply colored papillae. This combination is completely new in the Oriental hybrid divisions of lilies suited to forcing and to mass commercial cultivation. The variety is highly resistant to Fusarium disease and shows tolerance of virus. The bulbs may be precooled and forced for cut-flower production under a wide range of temperature and light levels. The clone is vigorous and is a good grower and propagator.

1 Drawing Sheet

BACKGROUND OF THE INVENTION

My new variety of lily plant originated as a seedling which first flowered in Woodland, Wash., in 1987. The breeding efforts had as their objective the production of large-flowered completely upfacing Oriental hybrids in a variety of shades of pink, with deeply pigmented papillae, suited to forcing into flower out of season, heretofore unknown in the lily breeding art.

I achieved the desired objective by intercrossing unnamed upright and semi-upright Oriental seedlings which carried pink flower color and were also suited to forcing for year-round use as cut-flowers. The unnamed Oriental seedlings which were the parents of 'Rose Paramount' were produced by me, from a series of crosses among seedlings which were selected in my fields from large seedling populations of my own crosses. The original crosses came from material unique to my own breeding lines and not available in the trade. The field-selected seedlings were genetically very diverse, and 100 seedlings were selected for their outstanding vigor, stem length, pink flower color, and upfacing or semi-upfacing flower orientation. These were forced into flower under glass, and the 25 seedlings which showed the best forcing performance were then randomly intercrossed to produce a large quantity of seed. This seed was grown to flowering size, producing a large population of seedlings, from which the best 100 were again selected for vigor, stem length, pink flower color, and upfacing or semi-upfacing flower orientation. These were subsequently tested for their forcing performance, and 'Rose Paramount' was selected as one of the seedlings best suited for forcing as a cut-flower.

The flowers of my new lily are characterized by a completely upfacing orientation, large size, broad tepals with inner tepals noticeably overlapping, unusually thick substance, distinctive even medium pink, deep pink papillae confined to the basal third of the tepals, and green nectaries with yellow papillose margins, a combination unique among Oriental hybrid lilies. The variety possesses unusually strong, stout stems. In addition, the clone possesses to a high degree desirable characteristics of hybrid vigor. The clone is a good grower and propagator, as observed as Woodland, Wash.

My new variety of lily plant has been asexually reproduced by me and under my direction at Woodland, Wash. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive completely upfacing flowers with even medium pink coloration, deep pink papillae confined to the basal third of the tepals, and green nectaries with yellow papillose margins.

DESCRIPTION OF THE NEW VARIETY

The following is a detailed description of my new variety of Oriental hybrid lily, with nomenclature according to the *International Lily Register* (Royal Horticultural Society of London, Second Edition, 1969), and with color designations according to the Color Chart of The Royal Horticultural Society, published by the Society in 1966.

The Plant

Origin: Seedling.

Seed parent: Selected unnamed Oriental hybrid seedling.

Pollen parent: Selected unnamed Oriental hybrid seedling.

Commercial classification: Hybrid Lilium clone.

Horticultural classification: Division VII-B, bowl-shaped Oriental hybrid lily, according to the Horticultural Classification of Lilies, Royal Horticultural Society of London.

Form: Single stem, erect and stately.

Height: 80 to 125 cm from bulbs 14 to 18 cm in circumference, provided their light levels are adequate; low light levels may cause "stretching."
Growth: Vigorous and upright.
Foliage quantity: Abundant.
Size of leaf: Broad, 4 to 7 cm wide×10 to 14 cm long.
Shape of leaf: Lanceolate (pointed).
Texture: Leathery and glossy.
Color: Medium green, lighter on lower side.
Bulb:
*Size.*—Any size, ranging to 25 cm circumference commercially.
*Color.*—White, with flushes of pink or yellow after exposure to light.

The Bud

Form: Obtuse, ovoid, and long.
Size: 12 to 16 cm long and 10 to 14 cm in circumference just prior to opening.
Opening: Bud opens slowly, in response to morning light, this takes about one hour.
Color: Soft pink (R.H.S. CC red-purple 62 B), just prior to opening, shading into soft green along the midribs.
Peduncle: Averages 4 to 6 cm, but it may elongate if light levels are too low or if bulbs have been improperly stored prior to forcing. Color is medium to dark green with very light plum overlay.

The Flower

Blooming habit: Annually in midseason; flowers once and profusely.
Size: Flowers are large-sized, averaging 20 to 28 cm in diameter, reflexing at the tips on the second day to 18 to 22 cm in diameter. The tepals are broad: outer tepals are 3 to 4 cm wide, and inner tepals are 5 to 6.25 cm wide. The inner tepals overlap noticeably.
Borne: In a single racemic inflorescence producing 4 to 10 flowers from a bulb 14 to 16 cm in circumference. Inflorescence is compact and pyramidal.
Shape: Form a broad bowl shape by the second day after opening, with the "bowl" 4 to 8 cm deep.
Tepalage: Typical of genus Lilium, with 6 imbricated tepals.
Tepal:
*Color.*—R.H.S. CC red-purple 62 A/B, very evenly distributed. The pink color may decrease with high temperatures and low light levels, and it may deepen slightly with cool temperatures and high light levels.
Spotting.—The basal third of each tepal is spotted with deep magenta rose (R.H.S. CC red-purple 59 B -63 B) papillae of moderate size. Papillae immediately adjacent to the nectaries are extremely elongated; these papillae may be white or yellow at the base and white or pink at their extreme tips.
Longevity.—Tepals stay on stems about three weeks.
Nectaries: Green with noticeable yellow (RHS 3 B/C) margins.
Pedicel:
*Length.*—Average 6 to 10 cm long.
*Color.*—Medium to dark green with very light plum overlay.
*Form.*—Sturdy, flexible, and noticeably ascending.
Color changes: Flowers become slightly lighter and a more lavender-toned pink as the flowers age. Low light levels and extreme heat may cause the pink pigmentation to decrease.
Appearance: Flower is shiny.
Disease resistance: The flower and plant are resistant to disease; in particular, they are resistant to Fusarium bulb rot and Botrytis blight.
Fragrance: Light sweet fragrance
Lasting quality: The flower is long lasting, both on the plant and as a cut-flower.

The Reproductive Organs

Stamens: Arrangement typical of genus Lilium. Six stamens with soft yellow-green to white filaments 8 to 10 cm long.
Pollen and anthers (dehisced): R.H.S. CC greyed red 180 A to greyed purple 183 A.
Pistil: One in number, 10 to 12 cm long.
Stigma: R.H.S. CC greyed purple 186 B/C; medium in size.
Characteristics of ovary: Characteristic of genus Lilium.

The Fruit

Fertility: The fruit bears fertile seed.
Shape: Ovoid.
Color at maturity: Soft brown, sometimes overlaid with soft plum.

My new variety of Oriental hybrid lily most nearly resembles 'Le Reve' (U.S. Plant No. 5,189), but it has thicker flowers with inner tepals which overlap conspicuously, a deeper bowl shape, and a more evenly distributed medium pink flower coloration. The flowers are completely upfacing and the pedicels are noticeably ascending. 'Rose Paramount' gives a much more reliable forcing performance under a wider range of light and temperature conditions than does 'Le Reve.' It somewhat resembles 'Acapulco' (U.S. Plant Pat. No. 8,313), but it has lighter pink and more even flower coloration, broadly overlapping inner flower tepals, shorter pedicels, and a more compact inflorescence.

I claim:

1. A new and distinctive variety of Oriental hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season under a wide range of light and temperature conditions; and in particular by its unique completely upfacing flowers with their evenly distributed medium pink coloration, deep magenta rose papillae on the basal third of the tepals only, green nectaries with yellow margins, and broadly overlapping inner tepals, a combination unique among Oriental hybrid lilies suited to forcing and to mass commercial cultivation.

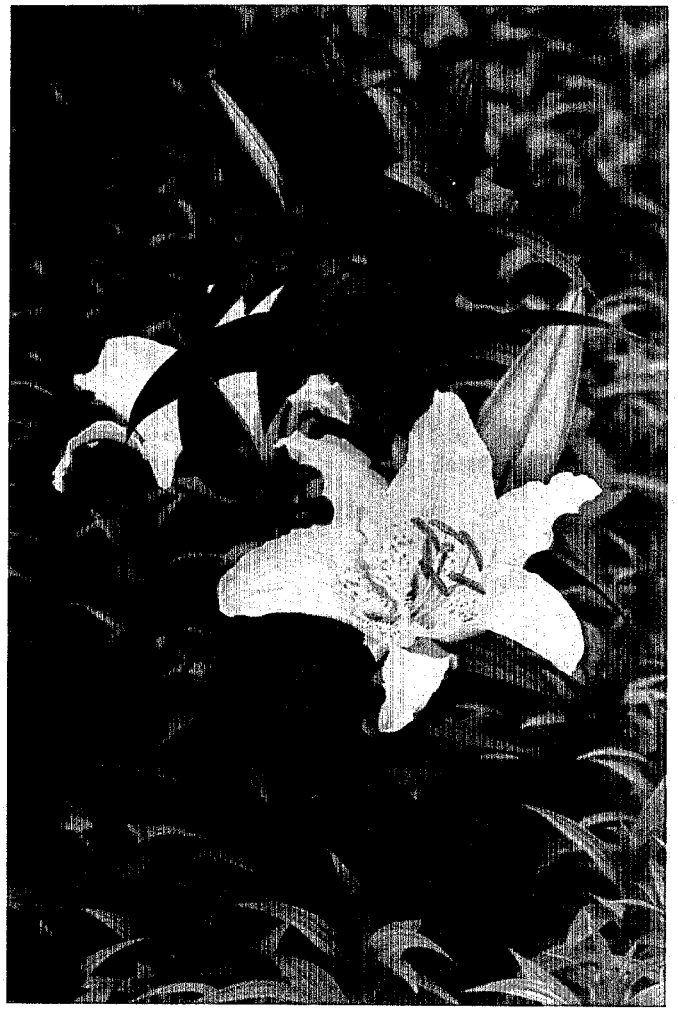

* * * * *